(12) United States Patent
Burkholz et al.

(10) Patent No.: US 9,750,928 B2
(45) Date of Patent: Sep. 5, 2017

(54) BLOOD CONTROL IV CATHETER WITH STATIONARY SEPTUM ACTIVATOR

(71) Applicant: Becton, Dickinson and Company, Franklin Lakes, NJ (US)

(72) Inventors: Jonathan Karl Burkholz, Salt Lake City, UT (US); S. Ray Isaacson, Roy, UT (US); Marty L. Stout, South Jordan, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/766,550

(22) Filed: Feb. 13, 2013

(65) Prior Publication Data

US 2014/0228775 A1    Aug. 14, 2014

(51) Int. Cl.
| | |
|---|---|
| A61M 39/16 | (2006.01) |
| A61M 25/00 | (2006.01) |
| A61M 25/06 | (2006.01) |
| A61M 39/06 | (2006.01) |

(52) U.S. Cl.
CPC ...... *A61M 39/162* (2013.01); *A61M 25/0097* (2013.01); *A61M 39/0693* (2013.01); *A61M 25/0606* (2013.01); *A61M 39/0606* (2013.01); *A61M 2039/064* (2013.01); *A61M 2039/068* (2013.01)

(58) Field of Classification Search
USPC .............. 604/86, 88, 148, 201, 244, 415, 87, 604/167.02, 202, 205, 288.02, 265
See application file for complete search history.

(56) References Cited

U.S. PATENT DOCUMENTS

| | | |
|---|---|---|
| 3,223,629 A | 12/1965 | Loeffler |
| 3,695,921 A | 10/1972 | Shepherd et al. |
| 3,986,508 A | 10/1976 | Barrington |
| 4,170,996 A | 10/1979 | Wu |
| 4,334,551 A | 6/1982 | Pfister |
| 4,339,336 A | 7/1982 | Hammond et al. |
| 4,387,879 A | 6/1983 | Tauschinski |

(Continued)

FOREIGN PATENT DOCUMENTS

| | | |
|---|---|---|
| CA | 1331333 C | 8/1994 |
| CA | 2133053 A1 | 3/1995 |

(Continued)

OTHER PUBLICATIONS

"ComfortCoat Hydrophilic Coating," DSM in Medical, http://www.dsm.com/en_US/medical/public/home/pages/product-coating-comfortcoat.jsp, Updated Jan. 11, 2013, Printed Apr. 22, 2013.

(Continued)

*Primary Examiner* — Scott Medway
(74) *Attorney, Agent, or Firm* — Jeanne Lukasavage; Craig Metcalf; Kirton McConkie (57) ABSTRACT

A system and method is provided for applying an anti-pathogenic material to various surfaces of a medical device, wherein the method includes identifying various surfaces of the medical tests which include noncritical dimensions, and limiting the application of the anti-pathogenic material to those surfaces. Some aspects of the invention further include the application of an anti-pathogenic lubricant material to various parts or components of a medical device to reduce friction.

14 Claims, 8 Drawing Sheets

(56) References Cited

U.S. PATENT DOCUMENTS

| | | | |
|---|---|---|---|
| 4,449,693 A | 5/1984 | Gereg | |
| 4,512,766 A | 4/1985 | Vailancourt | |
| 4,584,192 A | 4/1986 | Dell et al. | |
| 4,592,920 A | 6/1986 | Murtfeldt | |
| 4,603,152 A | 7/1986 | Laurin et al. | |
| 4,629,743 A | 12/1986 | Hong | |
| 4,629,746 A | 12/1986 | Michl et al. | |
| 4,642,126 A | 2/1987 | Zador et al. | |
| 4,676,782 A | 6/1987 | Yamamoto et al. | |
| 4,677,143 A | 6/1987 | Laurin et al. | |
| 4,716,032 A | 12/1987 | Westfall et al. | |
| 4,758,225 A | 7/1988 | Cox et al. | |
| 4,798,594 A | 1/1989 | Hillstead | |
| 4,842,591 A * | 6/1989 | Luther | 604/537 |
| 4,874,377 A * | 10/1989 | Newgard et al. | 604/167.02 |
| 4,895,566 A | 1/1990 | Lee | |
| 4,897,427 A | 1/1990 | Barnavon et al. | |
| 4,915,934 A | 4/1990 | Tomlinson | |
| 4,917,668 A | 4/1990 | Haindl | |
| 4,925,668 A | 5/1990 | Khan et al. | |
| 4,933,178 A | 6/1990 | Capelli | |
| 4,935,010 A | 6/1990 | Cox et al. | |
| 4,950,257 A | 8/1990 | Hibbs et al. | |
| 4,955,890 A | 9/1990 | Yamamoto et al. | |
| 4,985,399 A | 1/1991 | Matsuda et al. | |
| 4,990,357 A | 2/1991 | Karakelle et al. | |
| 5,019,096 A | 5/1991 | Fox, Jr. et al. | |
| 5,023,082 A | 6/1991 | Friedman et al. | |
| 5,030,665 A | 7/1991 | Lee et al. | |
| 5,041,097 A | 8/1991 | Johnson | |
| 5,053,014 A * | 10/1991 | Van Heugten | 604/167.03 |
| 5,062,836 A | 11/1991 | Wendell | |
| 5,064,416 A * | 11/1991 | Newgard et al. | 604/167.03 |
| 5,077,352 A | 12/1991 | Elton | |
| 5,078,703 A | 1/1992 | Bryant | |
| 5,084,023 A | 1/1992 | Lemieux | |
| 5,085,645 A * | 2/1992 | Purdy et al. | 604/167.03 |
| 5,098,410 A | 3/1992 | Kerby et al. | |
| 5,108,374 A | 4/1992 | Lemieux | |
| 5,127,905 A | 7/1992 | Lemieux | |
| 5,154,703 A * | 10/1992 | Bonaldo | 604/244 |
| 5,156,596 A * | 10/1992 | Balbierz et al. | 604/164.11 |
| 5,217,493 A | 6/1993 | Raad et al. | |
| 5,234,410 A | 8/1993 | Graham et al. | |
| 5,242,425 A * | 9/1993 | White et al. | 604/256 |
| 5,290,246 A | 3/1994 | Yamamoto et al. | |
| 5,295,969 A | 3/1994 | Fischell et al. | |
| 5,330,435 A * | 7/1994 | Vaillancourt | 604/167.01 |
| 5,350,363 A | 9/1994 | Goode et al. | |
| 5,352,205 A | 10/1994 | Dales et al. | |
| 5,357,636 A | 10/1994 | Dresdner, Jr. et al. | |
| 5,366,505 A | 11/1994 | Farber | |
| 5,405,323 A | 4/1995 | Rogers et al. | |
| 5,456,675 A | 10/1995 | Wolbring et al. | |
| 5,456,948 A | 10/1995 | Mathisen et al. | |
| 5,487,728 A | 1/1996 | Vaillancourt | |
| 5,512,199 A | 4/1996 | Khan et al. | |
| 5,520,666 A | 5/1996 | Choudhury et al. | |
| 5,540,661 A * | 7/1996 | Tomisaka et al. | 604/265 |
| 5,547,662 A | 8/1996 | Khan et al. | |
| 5,549,566 A | 8/1996 | Elias et al. | |
| 5,549,577 A | 8/1996 | Siegel et al. | |
| 5,575,769 A | 11/1996 | Vaillancourt | |
| 5,613,663 A | 3/1997 | Schmidt et al. | |
| 5,616,338 A | 4/1997 | Fox, Jr. et al. | |
| 5,620,434 A * | 4/1997 | Brony | 604/406 |
| 5,629,006 A | 5/1997 | Hoang et al. | |
| 5,638,812 A | 6/1997 | Turner | |
| 5,651,772 A | 7/1997 | Arnett | |
| 5,653,695 A | 8/1997 | Hopkins et al. | |
| 5,657,963 A | 8/1997 | Hinchliffe et al. | |
| 5,688,747 A | 11/1997 | Khan et al. | |
| 5,697,915 A | 12/1997 | Lynn | |
| 5,698,229 A | 12/1997 | Ohsumi et al. | |
| 5,712,229 A | 1/1998 | Hopkins et al. | |
| 5,716,406 A | 2/1998 | Farber | |
| 5,738,144 A | 4/1998 | Rogers | |
| 5,749,861 A | 5/1998 | Guala et al. | |
| 5,773,487 A | 6/1998 | Sokol | |
| 5,806,831 A | 9/1998 | Paradis | |
| 5,817,069 A * | 10/1998 | Arnett | 604/256 |
| 5,830,196 A | 11/1998 | Hicks | |
| 5,833,674 A * | 11/1998 | Turnbull et al. | 604/533 |
| 5,843,046 A * | 12/1998 | Motisi et al. | 604/256 |
| 5,861,440 A | 1/1999 | Gohla et al. | |
| 5,911,710 A | 6/1999 | Barry et al. | |
| 5,954,698 A | 9/1999 | Pike | |
| 5,967,490 A | 10/1999 | Pike | |
| 6,039,302 A | 3/2000 | Cote, Sr. et al. | |
| 6,046,143 A | 4/2000 | Khan et al. | |
| 6,051,609 A | 4/2000 | Yu et al. | |
| 6,077,244 A | 6/2000 | Botich et al. | |
| 6,117,108 A | 9/2000 | Woehr et al. | |
| 6,120,784 A | 9/2000 | Snyder, Jr. | |
| 6,127,320 A | 10/2000 | van Ooij et al. | |
| 6,165,168 A * | 12/2000 | Russo | 604/533 |
| 6,171,287 B1 | 1/2001 | Lynn et al. | |
| 6,242,526 B1 | 6/2001 | Siddiqui et al. | |
| 6,248,811 B1 | 6/2001 | Ottersbach et al. | |
| 6,273,869 B1 | 8/2001 | Vaillancourt | |
| 6,326,417 B1 | 12/2001 | Jia | |
| 6,337,357 B1 | 1/2002 | Fukunishi et al. | |
| 6,344,218 B1 | 2/2002 | Dodd et al. | |
| 6,353,041 B1 | 3/2002 | Qian | |
| 6,413,539 B1 | 7/2002 | Shalaby | |
| 6,475,434 B1 | 11/2002 | Darouiche | |
| 6,485,473 B1 | 11/2002 | Lynn | |
| 6,488,942 B1 | 12/2002 | Ingemann | |
| 6,492,445 B2 | 12/2002 | Siddiqui et al. | |
| 6,544,214 B1 | 4/2003 | Utterberg | |
| 6,575,960 B2 | 6/2003 | Becker et al. | |
| 6,576,633 B1 | 6/2003 | Young et al. | |
| 6,579,539 B2 | 6/2003 | Lawson et al. | |
| 6,595,981 B2 | 7/2003 | Huet | |
| 6,699,221 B2 * | 3/2004 | Vaillancourt | 604/167.01 |
| 6,719,726 B2 | 4/2004 | Meng et al. | |
| 6,719,991 B2 | 4/2004 | Darouiche et al. | |
| 6,723,350 B2 | 4/2004 | Burrell et al. | |
| 6,740,063 B2 | 5/2004 | Lynn | |
| 6,808,161 B1 * | 10/2004 | Hishikawa | 251/149.1 |
| 6,843,784 B2 | 1/2005 | Modak et al. | |
| 6,846,846 B2 | 1/2005 | Modak et al. | |
| 6,861,060 B1 | 3/2005 | Luriya et al. | |
| 6,883,778 B1 | 4/2005 | Newton et al. | |
| 6,887,270 B2 | 5/2005 | Miller et al. | |
| 6,896,889 B2 | 5/2005 | Chevalier et al. | |
| 7,008,404 B2 | 3/2006 | Nakajima | |
| 7,074,839 B2 | 7/2006 | Fansler et al. | |
| 7,098,256 B2 | 8/2006 | Ong et al. | |
| 7,179,849 B2 | 2/2007 | Terry | |
| 7,198,800 B1 | 4/2007 | Ko | |
| 7,232,428 B1 | 6/2007 | Inukai et al. | |
| 7,232,540 B2 | 6/2007 | Gould et al. | |
| 7,261,925 B2 | 8/2007 | Nesbitt | |
| 7,268,165 B2 | 9/2007 | Greten et al. | |
| 7,347,839 B2 | 3/2008 | Hiejima | |
| 7,374,798 B2 | 5/2008 | Choo et al. | |
| 7,396,346 B2 | 7/2008 | Nakajima | |
| 7,407,707 B2 | 8/2008 | Gould et al. | |
| 7,462,401 B2 | 12/2008 | Halfyard et al. | |
| 7,470,254 B2 | 12/2008 | Basta et al. | |
| 7,494,339 B2 | 2/2009 | Dias et al. | |
| 7,498,367 B2 | 3/2009 | Qian | |
| 7,514,477 B2 | 4/2009 | Klare et al. | |
| 7,608,082 B2 | 10/2009 | Cuevas et al. | |
| 7,704,935 B1 | 4/2010 | Davis et al. | |
| 7,736,339 B2 | 6/2010 | Woehr et al. | |
| 7,816,434 B2 | 10/2010 | Hackbarth et al. | |
| 7,871,649 B2 | 1/2011 | Modak et al. | |
| 7,874,467 B2 * | 1/2011 | Pardes et al. | 222/494 |
| 7,914,494 B2 * | 3/2011 | Hiejima | 604/167.04 |
| 7,981,475 B2 | 7/2011 | Takahashi | |
| 8,034,454 B2 | 10/2011 | Terry | |
| 8,034,455 B2 | 10/2011 | Wang et al. | |

(56) References Cited

U.S. PATENT DOCUMENTS

| | | |
|---|---|---|
| 8,067,402 B2 | 11/2011 | Whiteford et al. |
| 8,227,050 B1 | 7/2012 | O'Neil |
| 8,231,602 B2* | 7/2012 | Anderson et al. ............ 604/513 |
| 8,263,102 B2 | 9/2012 | Labrecque et al. |
| 8,268,381 B2 | 9/2012 | Whiteford et al. |
| 8,343,523 B2 | 1/2013 | Toreki et al. |
| 8,343,525 B2 | 1/2013 | Davis et al. |
| 8,357,119 B2* | 1/2013 | Stout et al. ................. 604/122 |
| 8,388,583 B2 | 3/2013 | Stout et al. |
| 8,414,547 B2 | 4/2013 | DiFiore et al. |
| 8,512,294 B2* | 8/2013 | Ou-Yang et al. ........ 604/167.04 |
| 8,622,995 B2 | 1/2014 | Ziebol et al. |
| 8,622,996 B2 | 1/2014 | Ziebol et al. |
| 8,728,030 B2 | 5/2014 | Woehr |
| 8,840,927 B2 | 9/2014 | DiTizio et al. |
| 9,078,441 B2 | 7/2015 | Raad |
| 9,138,252 B2 | 9/2015 | Bierman et al. |
| 2001/0010016 A1 | 7/2001 | Modak et al. |
| 2001/0016589 A1 | 8/2001 | Modak et al. |
| 2001/0018095 A1 | 8/2001 | Shlenker et al. |
| 2001/0032006 A1 | 10/2001 | Griffin, III et al. |
| 2001/0053895 A1 | 12/2001 | Vaillancourt |
| 2001/0056133 A1 | 12/2001 | Montgomery et al. |
| 2002/0009436 A1 | 1/2002 | Doyle et al. |
| 2002/0022660 A1 | 2/2002 | Jampani et al. |
| 2002/0028751 A1 | 3/2002 | Lokkesmoe et al. |
| 2002/0037260 A1 | 3/2002 | Budny et al. |
| 2002/0040092 A1 | 4/2002 | Siddiqui et al. |
| 2002/0064858 A1 | 5/2002 | Yacoby-Zeevi |
| 2002/0091424 A1 | 7/2002 | Biel |
| 2002/0119111 A1 | 8/2002 | Kilgour et al. |
| 2002/0133124 A1* | 9/2002 | Leinsing et al. ............. 604/256 |
| 2002/0144705 A1 | 10/2002 | Brattesani et al. |
| 2003/0023208 A1 | 1/2003 | Osypka et al. |
| 2003/0060804 A1* | 3/2003 | Vaillancourt ................ 604/533 |
| 2003/0068667 A1 | 4/2003 | Olson et al. |
| 2003/0072781 A1 | 4/2003 | Pelerin |
| 2003/0105143 A1 | 6/2003 | Ammendola et al. |
| 2003/0119932 A1 | 6/2003 | Al-Akhdar et al. |
| 2003/0134783 A1 | 7/2003 | Harshey et al. |
| 2003/0144362 A1 | 7/2003 | Utterberg et al. |
| 2003/0147932 A1 | 8/2003 | Nun et al. |
| 2003/0162839 A1 | 8/2003 | Symington et al. |
| 2003/0170308 A1 | 9/2003 | Cleary et al. |
| 2003/0176848 A1 | 9/2003 | Gibson et al. |
| 2003/0206875 A1 | 11/2003 | Budny et al. |
| 2003/0215433 A1 | 11/2003 | Kokai-Kun et al. |
| 2003/0224032 A1 | 12/2003 | Read et al. |
| 2004/0013574 A1 | 1/2004 | Conway |
| 2004/0013703 A1 | 1/2004 | Ralph et al. |
| 2004/0014864 A1 | 1/2004 | Milic et al. |
| 2004/0039349 A1 | 2/2004 | Modak et al. |
| 2004/0058829 A1 | 3/2004 | Hei et al. |
| 2004/0109852 A1 | 6/2004 | Xu |
| 2004/0115477 A1 | 6/2004 | Nesbitt |
| 2004/0132164 A1 | 7/2004 | Doyle et al. |
| 2004/0180829 A1 | 9/2004 | Bassler et al. |
| 2004/0185296 A1 | 9/2004 | Mazzanti |
| 2004/0230162 A1 | 11/2004 | Tan |
| 2004/0234475 A1 | 11/2004 | Lannibois-Drean et al. |
| 2005/0008671 A1 | 1/2005 | Van Antwerp |
| 2005/0048005 A1 | 3/2005 | Stockel |
| 2005/0048124 A1 | 3/2005 | Sarangapani |
| 2005/0059731 A1 | 3/2005 | Albrecht et al. |
| 2005/0080158 A1 | 4/2005 | Ong et al. |
| 2005/0100580 A1 | 5/2005 | Osborne et al. |
| 2005/0118239 A1 | 6/2005 | Sabesan |
| 2005/0124970 A1 | 6/2005 | Kunin et al. |
| 2005/0131356 A1 | 6/2005 | Ash et al. |
| 2005/0143286 A1 | 6/2005 | Singh et al. |
| 2005/0148928 A1 | 7/2005 | Molina et al. |
| 2005/0158253 A1 | 7/2005 | Budny et al. |
| 2005/0176905 A1 | 8/2005 | Moon et al. |
| 2005/0233950 A1 | 10/2005 | Madyastha |
| 2005/0265931 A1 | 12/2005 | Qian |
| 2006/0024372 A1* | 2/2006 | Utterberg et al. ............ 424/488 |
| 2006/0051385 A1 | 3/2006 | Scholz |
| 2006/0163515 A1 | 7/2006 | Ruschke |
| 2006/0165751 A1 | 7/2006 | Chudzik et al. |
| 2006/0165903 A1 | 7/2006 | Mazzanti |
| 2006/0177477 A1* | 8/2006 | Ash et al. .................... 424/423 |
| 2006/0239954 A1 | 10/2006 | Sancho |
| 2006/0258780 A1 | 11/2006 | Chaussade et al. |
| 2006/0281663 A1 | 12/2006 | Asmus |
| 2007/0000407 A1 | 1/2007 | Leong |
| 2007/0083157 A1 | 4/2007 | Belley et al. |
| 2007/0083162 A1 | 4/2007 | O'Reagan et al. |
| 2007/0112112 A1 | 5/2007 | Kerschner et al. |
| 2007/0112146 A1 | 5/2007 | Falk et al. |
| 2007/0129690 A1 | 6/2007 | Rosenblatt et al. |
| 2007/0141524 A1 | 6/2007 | Brennan et al. |
| 2007/0160547 A1 | 7/2007 | Duffy et al. |
| 2007/0166344 A1 | 7/2007 | Qu et al. |
| 2007/0202177 A1 | 8/2007 | Hoang |
| 2007/0203574 A1 | 8/2007 | McGrath et al. |
| 2007/0225179 A1 | 9/2007 | Schutz et al. |
| 2007/0233007 A1* | 10/2007 | Adams ..................... 604/168.01 |
| 2007/0275101 A1 | 11/2007 | Lu et al. |
| 2007/0281198 A1 | 12/2007 | Lousenberg |
| 2008/0026026 A1 | 1/2008 | Lu et al. |
| 2008/0051737 A1 | 2/2008 | Paul et al. |
| 2008/0075761 A1 | 3/2008 | Modak et al. |
| 2008/0108944 A1 | 5/2008 | Woehr et al. |
| 2008/0119789 A1 | 5/2008 | Kaemmerer |
| 2008/0161763 A1 | 7/2008 | Harding et al. |
| 2008/0182921 A1 | 7/2008 | Suh et al. |
| 2008/0194707 A1 | 8/2008 | Potter |
| 2009/0012220 A1 | 1/2009 | Yamane et al. |
| 2009/0036768 A1 | 2/2009 | Seehusen et al. |
| 2009/0101152 A1 | 4/2009 | Burk et al. |
| 2009/0110844 A1 | 4/2009 | Platzer et al. |
| 2009/0114327 A1 | 5/2009 | Breunig |
| 2009/0117164 A1 | 5/2009 | Toreki et al. |
| 2009/0125118 A1 | 5/2009 | Gong |
| 2009/0162530 A1 | 6/2009 | Nesbitt |
| 2009/0176907 A1 | 7/2009 | Subramanian et al. |
| 2009/0188559 A1 | 7/2009 | Nesbitt |
| 2009/0220739 A1 | 9/2009 | Chougule |
| 2009/0226541 A1 | 9/2009 | Scholz et al. |
| 2009/0281525 A1* | 11/2009 | Harding et al. ............. 604/537 |
| 2009/0317435 A1 | 12/2009 | Vandesteeg et al. |
| 2009/0324666 A1 | 12/2009 | Krongauz et al. |
| 2010/0106102 A1 | 4/2010 | Ziebol et al. |
| 2010/0135949 A1 | 6/2010 | Ou-Yang |
| 2010/0136209 A1 | 6/2010 | Ou-Yang et al. |
| 2010/0137379 A1 | 6/2010 | Ou-Yang |
| 2010/0137472 A1 | 6/2010 | Ou-Yang |
| 2010/0204648 A1 | 8/2010 | Stout et al. |
| 2010/0204675 A1 | 8/2010 | Woehr et al. |
| 2010/0222746 A1 | 9/2010 | Burkholz |
| 2011/0009831 A1 | 1/2011 | Burkholz et al. |
| 2011/0065798 A1 | 3/2011 | Hoang et al. |
| 2011/0146680 A1 | 6/2011 | Conway |
| 2011/0150958 A1 | 6/2011 | Davis et al. |
| 2011/0160663 A1 | 6/2011 | Stout et al. |
| 2011/0218529 A1 | 9/2011 | Garcia et al. |
| 2011/0301553 A1 | 12/2011 | Goral et al. |
| 2011/0319825 A1 | 12/2011 | Goral et al. |
| 2012/0078203 A1 | 3/2012 | Gaube et al. |
| 2012/0083750 A1 | 4/2012 | Sansoucy |
| 2012/0103448 A1 | 5/2012 | Hopf et al. |
| 2013/0165483 A1* | 6/2013 | Isaacson et al. ............ 604/256 |
| 2013/0196079 A1 | 8/2013 | Schwalm et al. |
| 2013/0245568 A1 | 9/2013 | Kerr |
| 2013/0274686 A1 | 10/2013 | Ziebol et al. |

FOREIGN PATENT DOCUMENTS

| | | |
|---|---|---|
| CN | 1187598 A1 | 7/1998 |
| CN | 1526771 A | 9/2004 |
| CN | 101353545 A | 1/2009 |
| CN | 102070983 A | 5/2011 |
| DE | 4011867 A1 | 10/1991 |
| EP | 0 036 294 A2 | 9/1981 |

(56) References Cited

FOREIGN PATENT DOCUMENTS

| | | |
|---|---|---|
| EP | 0 070 087 A1 | 1/1983 |
| EP | 0 338 418 A1 | 10/1989 |
| EP | 0 370 997 A2 | 5/1990 |
| EP | 0 379 271 A2 | 7/1990 |
| EP | 0 396 431 A1 | 11/1990 |
| EP | 0 414 997 A1 | 3/1991 |
| EP | 0 778 337 A2 | 11/1997 |
| EP | 0 992 252 A2 | 4/2000 |
| JP | 05-277434 | 10/1993 |
| JP | H07-47435 A | 2/1995 |
| JP | H07-051651 | 2/1995 |
| JP | H08-209064 | 8/1996 |
| JP | 8-311373 A | 11/1996 |
| JP | 09-151262 | 6/1997 |
| JP | H09-157548 | 6/1997 |
| JP | H09-176677 A | 7/1997 |
| JP | H10-231 A | 1/1998 |
| JP | H11-322560 A | 11/1999 |
| JP | 2000-178475 A1 | 6/2000 |
| JP | 2000-264803 A | 9/2000 |
| JP | 2001-072438 A1 | 3/2001 |
| JP | 2002-282762 | 10/2002 |
| JP | 2003-342402 | 12/2003 |
| JP | 2004-043669 A | 2/2004 |
| JP | 2005-028209 A | 2/2005 |
| JP | 2005-515838 A | 6/2005 |
| JP | 2005-520912 A | 7/2005 |
| JP | 2007-016096 A | 1/2007 |
| JP | 2010-536836 A | 12/2010 |
| KR | 20020066429 A1 | 8/2002 |
| KR | 20080039460 A | 5/2008 |
| WO | 94/22522 A1 | 10/1994 |
| WO | 95/21648 A1 | 8/1995 |
| WO | 96/40359 A1 | 12/1996 |
| WO | 98/58690 | 12/1998 |
| WO | 98/58989 | 12/1998 |
| WO | 99/32168 | 7/1999 |
| WO | 99/34849 A1 | 7/1999 |
| WO | 99/36490 A1 | 7/1999 |
| WO | 99/43971 A1 | 9/1999 |
| WO | 00/66189 | 11/2000 |
| WO | 00/74743 A | 12/2000 |
| WO | 01/95862 | 12/2001 |
| WO | 2004/108091 A2 | 12/2004 |
| WO | 2005/037340 A2 | 4/2005 |
| WO | 2006/056482 A1 | 6/2006 |
| WO | 2006/074666 A2 | 7/2006 |
| WO | 2006/088288 A1 | 8/2006 |
| WO | 2006/099358 A2 | 9/2006 |
| WO | 2007/064835 A2 | 6/2007 |
| WO | 2007/095576 A2 | 8/2007 |
| WO | 2007/100653 A2 | 9/2007 |
| WO | 2007/100776 A2 | 9/2007 |
| WO | 2008/014438 A2 | 1/2008 |
| WO | 2008014447 A2 | 1/2008 |
| WO | 2008/031601 A1 | 3/2008 |
| WO | 2008/045761 A2 | 4/2008 |
| WO | 2008/128896 A2 | 10/2008 |
| WO | 2008/132045 A2 | 11/2008 |
| WO | 2009/070227 A1 | 6/2009 |
| WO | 2011/005951 A2 | 1/2011 |
| WO | 2011/034675 A2 | 3/2011 |
| WO | 2011/048204 A2 | 4/2011 |
| WO | 2011/118680 A1 | 9/2011 |
| WO | 2012/036916 A1 | 3/2012 |
| WO | 2013/009998 A3 | 1/2013 |
| WO | 2013/134421 A1 | 9/2013 |

OTHER PUBLICATIONS

"Lubricent—Lubricious Hydrophillic Coatings for Medical Devices," Harland Medical Systems, http://www.harlandmedical.com/index.php/materials/lubricent.html, pp. 1-2, Printed Apr. 22, 2013.

"UV & EB Cure," Xiper Innovations, Inc., http://xiperinnovations.com/uv_eb_cure, Printed Apr. 22, 2013.

Cabot Corporation, "Using Silicas and Aluminas in Coatings,", www.cabot-corp.com/Silicas-And-Aluminas/Coatings, downloaded from the internet on Apr. 26, 2011.

McDonnell, G., Russell, A.D. Antiseptics and Disinfectants: Activity, Action, and Resistance. Clinical Microbiology Reviews, (1999) 12(1), pp. 149-179.

Ciba Irgacure 500 data sheet from Ciba Specialty Chemicals. Online. Retrieved on Dec. 12, 2015. URL <http://www.conquimica.com/wp-content/uploads/2015/06/ft_irgacure_500.pdf>.

Elson Silva, PhD, "Respecting Hydrology Science in the Patenting System," pp. 1-7, Jan. 13, 2011.

Gama Healthcare, Clinell Alcoholic 2% Chlorhexidine, http://www.gamahealthcare.com/clinellaca2c.html, pp. 1-3, Nov. 7, 2008.

Enturia, ChloraPrep, http://www.enturia.com/products/chloraPrep-product.html, pp. 1-3, Oct. 31, 2008.

Sage Products, Inc., Address Multi-Drug Resistant Organism on the Skin with Early Preop Prep, http://www.sageproducts.com/products/ssi-prevention.cfm, 1 page, Oct. 31, 2008.

Sage Products, Inc., Preoperative Skin Preparation and Perioperative Oral Care for the Short-Term Ventilated Patient, http://www.sageproducts.com/products/ssi-vap-prevention.cfm, 1 page, Oct. 31, 2008.

Sage Products, Inc., Preoperative Skin Preparation for the Surgical Patient, http://www.sageproducts.com/products/skin-prep.cfm, 1 page, Oct. 31, 2008.

* cited by examiner

BLOOD CONTROL IV CATHETER WITH STATIONARY SEPTUM ACTIVATOR

BACKGROUND OF THE INVENTION

The present invention relates to blood control intravenous (IV) catheter having an integrated, stationary septum activator. Further, the present invention relates to systems and methods for coating various surfaces of the blood control IV catheter with an anti-pathogenic material. Further still, the present invention relates to systems and methods for coating various interfacing surfaces between a catheter adapter, the stationary septum activator, and a blood control septum of the blood control IV catheter with an anti-pathogenic lubricant material to reduce friction therebetween.

A formidable challenge of modern medical treatment is control of infection in the spread of pathogenic organisms. One area where this challenge is constantly presented is in infusion therapy of various types. Infusion therapy is one of the most common healthcare procedures. Hospitalized, home care, and other patients receive fluids, pharmaceuticals, and blood products via a vascular access device inserted into the vascular system of the patient. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access the patient's peripheral or central vasculature. The vascular access device may be indwelling for short-term (days), moderate term (weeks), or long-term (months two years). The vascular access device may be used for continuous infusion therapy or for intermittent therapy.

A common vascular access device comprises a plastic catheter inserted into a patient's vein. The catheter length may vary from a few centimeters or peripheral access, to many centimeters for central access and may include devices such as peripherally inserted central catheters (PICC). The catheter may be inserted transcutaneously or may be surgically implanted beneath the patient's skin. The catheter, or any other vascular access device attached thereto, may have a single lumen or multiple lumens for infusion of many fluids simultaneously.

A common vascular access device comprises a blood control septum that controls flow of blood and other fluids through the vascular access device. In some instances the vascular access device further includes a septum actuator that is slidably housed within the vascular access device. The septum actuator may be advanced through the blood control septum to enable blood or other fluids to bypass the septum. Generally, the septum actuator is retained within the vascular access device by providing a channel or other feature in which the septum actuator is able to slide. These features require precise machining to achieve critical dimensions required to facilitate proper sliding movement of the septum actuator within the vascular access device.

A vascular access device may serve as a nidus, resulting in a disseminated BSI (blood stream infection). This may be caused by failure to regularly flush the device, a non-sterile insertion technique, or by pathogens that enter the fluid flow path through either end of the path subsequent to catheter insertion. When a vascular access device is contaminated, pathogens adhere to the vascular access device, colonize, and form a biofilm. The biofilm is resistant to most biocidal agents and provides a replenishing source of pathogens to enter a patient's bloodstream and cause a BSI.

One approach to preventing biofilm formation and patient infection is to provide an anti-pathogenic coating on various medical devices and components. However, some medical devices and components comprise materials or features which are incompatible with anti-pathogenic coatings. Thus, although methods exist for controlling blood flow through a vascular access device, and for providing an anti-pathogenic coating, challenges still exist. Accordingly, it would be an improvement in the art to augment or even replace current techniques with other techniques. Such techniques are disclosed herein.

BRIEF SUMMARY OF THE INVENTION

In order to overcome the limitations discussed above, the present invention relates to systems and methods for selectively coating non-dimensionally critical surfaces of medical devices which contact blood or other fluids as part of an infusion therapy.

Some implementations of the present invention include an infusion therapy medical device, such as a catheter assembly, having a blood control septum that is slidably housed within a fluid pathway of a catheter adapter. The blood control septum is configured to slide within the catheter adapter in both distal and proximal directions. The catheter adapter further includes a septum actuator that is secured to an inner surface of the catheter adapter at a fixed position. The septum actuator comprises probe portion that is concentrically or axially positioned within the fluid pathway of the catheter adapter at a position that is proximate to the blood control septum. As the blood control septum is slid in the distal direction, the probe portion of the septum actuator is advanced through the blood control septum to provide a pathway through the septum. Upon releasing the blood control septum, the septum is slid in the proximal direction such that the probe portion of the septum actuator is removed from the blood control septum. As such, the pathway through the blood control septum is closed to prevent further flow of fluid through the fluid pathway of the catheter adapter.

In some instances, the septum actuator comprises a molded feature of the inner surface of the catheter adapter. In other instances, the septum actuator comprises a separate unit that is fixedly coupled to the inner surface of the catheter adapter. Further, in some instances the septum actuator comprises a catheter wedge, wherein the septum actuator secures a base of a catheter into the catheter adapter, the probe portion of the septum actuator extending outwardly from the catheter wedge in a proximal direction. The septum actuators of the present invention further comprise a lumen that is in fluid communication with a fluid pathway of the catheter adapter when then septum actuator is advanced through the blood control septum. As such, fluid may flow through the fluid pathway of the catheter adapter and into the catheter via the lumen of the septum actuator.

In some instances, an anti-pathogenic material is applied to various surfaces of the catheter assembly to prevent colonization of pathogens within the fluid pathway of the device. In other instances, the anti-pathogenic material further comprises a lubricious agent to reduce friction between various components of the catheter assembly.

Some surfaces of the catheter assemblies of the present invention may include a noncritical dimension, wherein an anti-pathogenic material is applied to the surface. In some instances, an anti-pathogenic material is applied to one or more surfaces further comprises a portion of a fluid pathway through the device. Thus, the anti-pathogenic material is exposed to a fluid flowing through the fluid pathway of the device.

In some instances, an infusion therapy medical device is provided having a septum actuator which includes a probe portion configured to advance through a septum of the device upon actuation of the septum actuator. In some implementations, an anti-pathogenic material including a lubricant agent is applied to the probe portion of the septum actuator to reduce friction between the septum actuator and the septum during activation of the device. In other implementations, a rigid or semirigid anti-pathogenic material is applied to various surfaces of a base portion of the septum actuator.

Certain aspects of the present invention further include a color code system, whereby the identity of the anti-pathogenic material is identified based upon the color of the medical device.

Some aspects of the present invention include a medical device having a compatible surface which includes at least one mechanical bond whereby to facilitate binding between the surface and an anti-pathogenic material. Other aspects of the invention include providing a chemical bond between a compatible surface of a medical device and an anti-pathogenic material by surface cross-linking.

The present invention further includes various methods, techniques, and materials for identifying and coating surfaces of medical devices which include noncritical dimensions. Thus, an anti-pathogenic material may be applied to various surfaces within a medical device to reduce or eliminate pathogenic colonization and/or growth within the medical device thereby reducing the risk of pathogenic infection in patients.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiment of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

The term "proximal" is used to denote a portion of a device which, during normal use, is nearest the user and furthest from the patient. The term "distal" is used to denote a portion of a device which, during normal use, is farthest away from the user wielding the device and closest to the patient. The term "activation" of valve mechanism or septum is used to denote the action of opening or closing of such valve. For example, in some embodiments a catheter assembly is provided having a septum and a septum actuator, wherein the catheter assembly undergoes activation when the septum actuator is advanced through the septum, thereby providing a fluid pathway through the septum.

The term "critical dimension" is used to denote at least one of a height, a length, a width, a depth, a diameter, a thickness, an angle, a texture, or other structural feature of a surface of a medical device which is critical to the operation of the device. For example, in some embodiments a medical device may include a surface that is configured to interface with another device or component. As such, the surface may include a critical dimension that is configured to accommodate optimal interaction between the surface of the medical device and the interfacing device or component. Thus, in some embodiments a surface having a critical dimension must remain unmodified to preserve the intended and/or desired interaction of the surface in operating or using the medical device. Conversely, the term "noncritical dimension" is used to denote at least one of a height, a length, a width, a depth, a diameter, a thickness, an angle, a texture, or other structural feature of a medical device with is not critical to the operation of the device.

The terms "chemical bond" or "chemical bonding" are used to denote an attraction between atoms that allows an anti-pathogenic material to be applied to a desired surface of a medical device. For example, in some instances an anti-pathogenic material of the present invention is applied to the surface of an infusion therapy medical device via chemical bonding, wherein atoms of the anti-pathogenic material and atoms of the medical device are chemically attracted to one another. Chemical bonding may include any type of atomic bond, such as a covalent bond, an ionic bond, dipole-dipole interactions, London dispersion force, Van der Waals force, and hydrogen bonding. A chemical bond may further be denoted by the terms "cross-linking" or "surface cross-linking" for some embodiments.

The terms "mechanical bond" or "mechanical bonding" are used to denote a physical, non-chemical interaction between two or more materials. For example, in some instances a surface of a medical device is altered to include a texture, a groove and/or a ridge having a void which holds an anti-pathogenic material via capillary force. In other embodiments, a mechanical bond comprises a structural feature which provides increased surface area to a surface of a medical device. Further, in some embodiments a mechanical bond comprises a hydrophilic or hydrophobic material or coating that is applied to a surface of a medical device to attract an anti-pathogenic material. A mechanical bond may further be denoted by the term "mechanical interlock" for some embodiments.

The term "compatible surface" is used to denote a surface of a medical device which includes a noncritical dimension, or a surface which includes a critical dimension that will not be adversely affected by the addition of an anti-pathogenic material or coating.

The terms "rigid" or "semirigid" are used to denote a physical property of an anti-pathogenic material, wherein the material is deficient in, or devoid, or mostly devoid of flexibility. Alternatively, these terms are used to denote an inflexible or mostly inflexible physical property of an anti-pathogenic material when applied or coated onto a surface of a device. In some instances, the term semirigid is understood to describe a physical property of an anti-pathogenic material that is rigid to some degree or in some parts.

The term "modified rheology" is used to denote a physical property of an anti-pathogenic material, wherein the viscosity of an anti-pathogenic material is modified to prevent excessive migration of the anti-pathogenic material once applied to a surface of a device. As such, the modified rheology of the anti-pathogenic material prevents or substantially prevents contact between the anti-pathogenic material and adjacent surfaces or components.

The term "anti-pathogenic" is used to denote a material, such as a coating material, that acts against pathogens. Pathogens may include any organism or substance capable of causing a disease, such as bacteria, viruses, protozoa and fungi. Accordingly, an "anti-pathogenic material" as contemplated herein includes any material having properties for acting against a pathogen.

The present invention relates to blood control intravenous (IV) catheter having an integrated, stationary septum activator. Further, the present invention relates to systems and methods for coating various surfaces of the blood control IV catheter with an anti-pathogenic material. Further still, the present invention relates to systems and methods for coating various interfacing surfaces between a catheter adapter, the stationary septum activator, and a blood control septum of the blood control IV catheter with an anti-pathogenic lubricant material to reduce friction therebetween.

In some instances, an anti-pathogenic material is applied to a surface comprising a noncritical dimension. In some embodiments, an anti-pathogenic material is applied to one or more surfaces of a medical device prior to assembling the medical device. In other embodiments, an anti-pathogenic material is applied to first portion or component of a medical device and subsequently transferred to a second portion or component of the medical device through controlled migration of the anti-pathogenic material. In other instances, an anti-pathogenic material is intermixed with, or incorporated into the material of the medical device during a molding process of the device. Further, in some instances an anti-pathogenic material is applied to or incorporated into the material of a medical device such that the anti-pathogenic material elutes out from the material of the medical device into the immediate surroundings of the coated medical device. For example, in some embodiments a blood control IV catheter assembly is provided having lubricious and non-lubricious anti-pathogenic materials applied to surfaces of the catheter assembly having critical and non-critical dimensions, as taught in U.S. patent application Ser. No. 13/471,716, which is incorporated herein in its entirety.

In general, an anti-pathogenic material in accordance with the present invention may include any material having anti-pathogenic properties which may be applied to the surface of a medical device. For example, in some embodiments an anti-pathogenic material may include an antimicrobial composition, as taught in U.S. patent application Ser. Nos. 12/397,760, 11/829,010, 12/476,997, 12/490,235, and 12/831,880, each of which is incorporated herein by reference, in its entirety. In some embodiments, an anti-pathogenic material may further include an anti-infective or antimicrobial lubricant, as taught in U.S. patent application Ser. Nos. 12/436,404 and 12/561,863, each of which is incorporated herein in its entirety. Further, in some embodiments an anti-pathogenic material is incorporated into the material of a medical device, or a component thereof, such as a septum actuator.

Some embodiments of the present invention comprise a medical device or component having at least one surface that defines a portion of a fluid pathway through the medical device. The surface of the medical device is coated with an anti-pathogenic material to prevent colonization of pathogens on the coated surface.

The application of an anti-pathogenic material to the surface of a medical device results in the addition of a layer or "coat" of anti-pathogenic material to the surface. This layer of anti-pathogenic material has a dimension (i.e. thickness) which may affect a relationship between the coated surface and an interfacing or adjacent component of the medical device. For example, in some embodiments a medical device may include an aperture having a diameter to compatibly receive a second medical device, such as by a friction, press, mechanical or interference fit. As such, the diameter of the aperture includes critical dimensions to ensure proper fitting between the aperture and the second medical device. In this example, the addition of an anti-pathogenic material to the surface of the aperture will adjust the diameter of the aperture thereby adversely affecting the ability of the aperture to receive the second medical device.

Accordingly, in some embodiments of the present invention it is undesirable to modify or coat a surface of a medical device or component wherein the surface includes a critical dimension that will be adversely affected by the addition of the anti-pathogenic material. Thus, some embodiments of the present invention comprise a method for coating a medical device with an anti-pathogenic material, wherein the method includes a first step of identifying surfaces of the medical device which include noncritical dimensions. The method may further include a step whereby the surfaces having noncritical dimensions are then coated with an anti-pathogenic material. Some methods of the present invention may further include steps for identify and isolating surfaces of the medical device having critical dimensions, prior to coating the remaining surfaces with an anti-pathogenic material.

Figure 1:
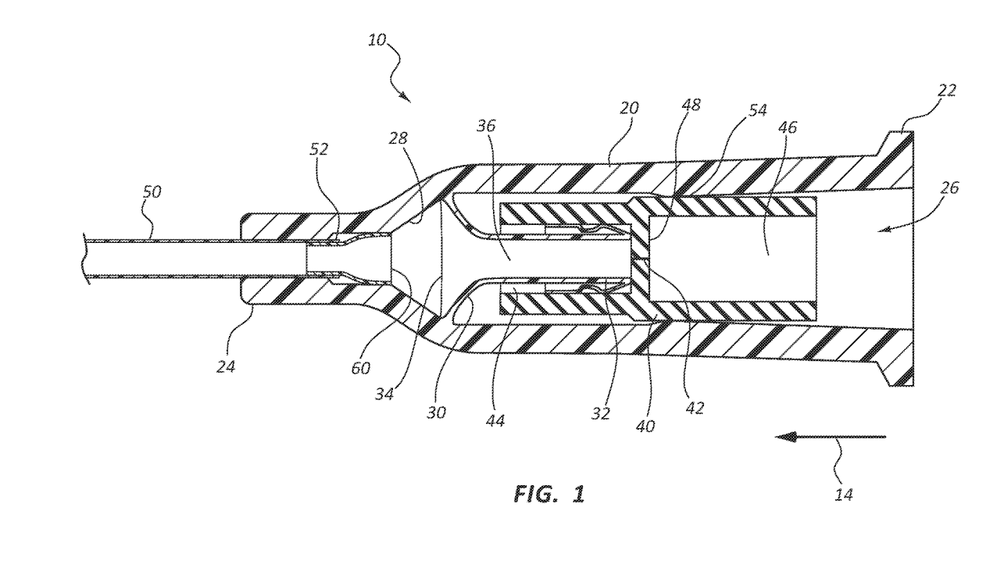
FIG. 1 is a cross-section side view of a catheter assembly comprising an integrated, stationary septum actuator prior to activation in accordance with a representative embodiment of the present invention.

Referring now to FIG. 1, a blood control catheter assembly 10 is shown. Generally, blood control catheter assembly 10 comprises a catheter adapter 20 having a proximal end 22, a distal end 24 and a fluid pathway 26 extending therebetween. In some instances, proximal end 22 comprises a feature for coupling an external device to catheter adapter 20. For example, in some embodiments proximal end 22 comprises a set of threads to compatibly receive a Luer adapter.

The catheter adapter 20 generally has a tubular shape. An inner surface 28 is tapered toward distal end 24, with a gradually reduced diameter. Catheter adapter 20 is preferably of a transparent or semi-transparent material so as to show the interior, enabling checking of movement inside. Suitable materials for catheter adapter 20 include, but are not limited to, thermoplastic polymeric resins such as polycarbonate, polystyrene, polypropylene and the like.

Catheter assembly 10 further comprises a catheter 50. A base portion 52 of catheter 50 is inserted into an opening of distal end 24 and secured via a press-fitted wedge 60. In some embodiments, it is preferred that a lubricating coating is provided to the outer surface of catheter 50 to reduce resistance caused by insertion through skin or into a blood vessel. Suitable materials for catheter 50 include, but are not limited to, thermoplastic resins such as fluorinated ethylene propylene (FEP), polytetrafluoroethylene (PTFE), polyurethane and the like. In some embodiments, catheter 40 is formed from a thermoplastic hydrophilic polyurethane that softens with exposure to physiological conditions present in the patient's body.

Catheter assembly 10 may further include features for use with an over-the-needle catheter assembly. For example, a flexible or semi flexible polymer catheter may be used in combination with a rigid introducer needle to enable insertion of the catheter into the vasculature of a patient. Surgically implanted catheters may also be used.

Once inserted into a patient, catheter 50 and catheter adapter 20 provide a fluid conduit to facilitate delivery of a fluid to and/or retrieval of a fluid from a patient, as required by a desired infusion procedure. Thus, in some embodiments the material of the catheter 50 and the catheter adapter 20 are selected to be compatible with bio-fluids and medicaments commonly used in infusion procedures. Additionally, in some embodiments a portion of the catheter 50 and/or catheter adapter 20 is configured for use in conjunction with a section of intravenous tubing (not shown) to further facilitate delivery of a fluid to or removal of a fluid from a patient.

Catheter adapter 20 further comprises a septum actuator 30. Septum actuator 30 is fixedly secured within fluid pathway 26 and positioned such that a blood control septum 40 may be slid in a distal direction 14 within fluid pathway 26 and be biased into an open position by septum actuator 30. In some instances, septum actuator comprises a molded, internal feature of catheter adapter 20. For example, septum actuator 20 may include a base 34 that is fused to or formed as part of inner surface 28. Alternatively, septum actuator 20 may comprise a separate unit having a base 34 that is fixedly secured within an annular groove 29 of inner surface 28, as shown in FIG. 2.

Figure 2:
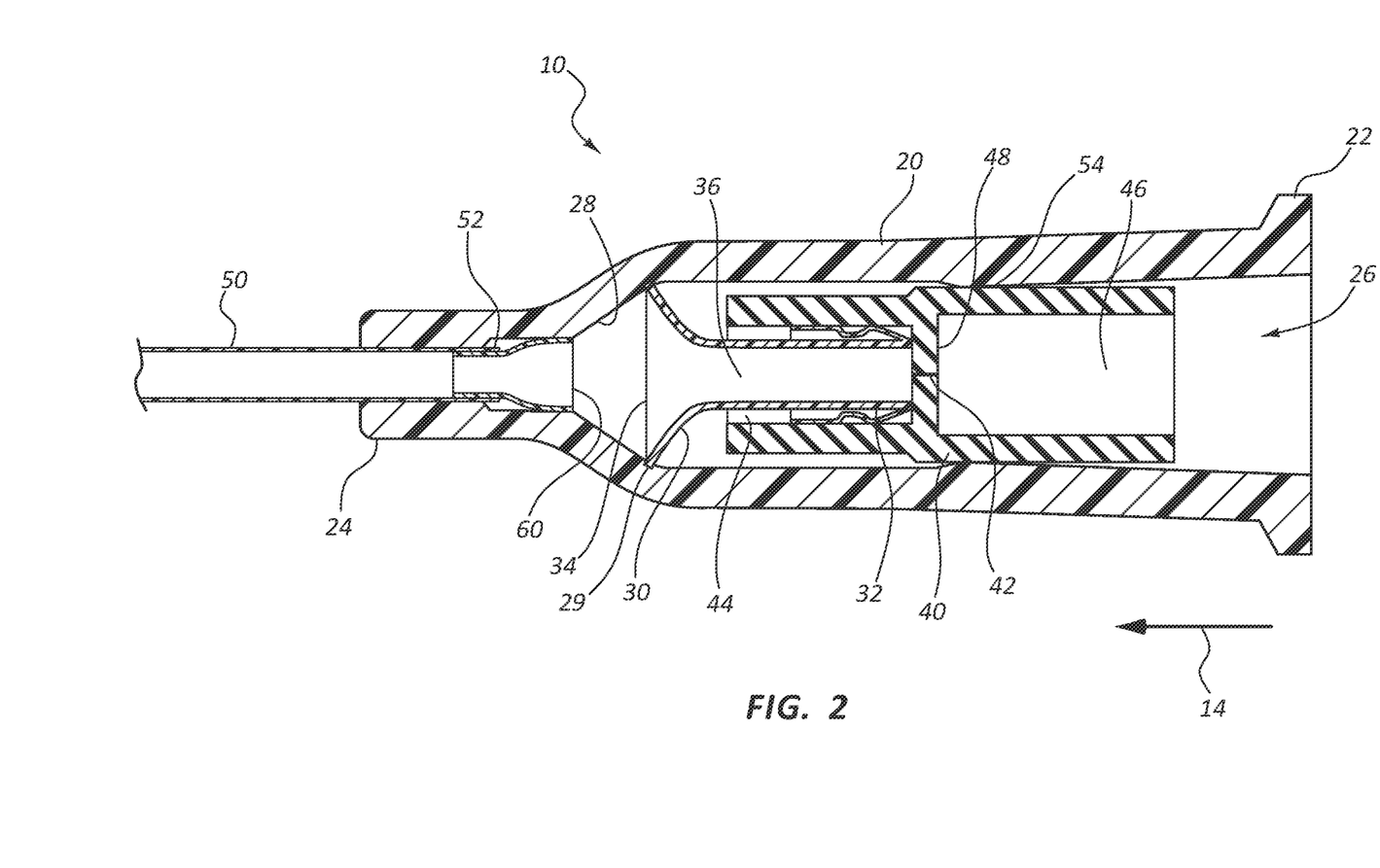
FIG. 2 is a cross-section side view of a catheter assembly comprising a septum actuator that is fixedly coupled to the catheter adapter via an annular groove in accordance with a representative embodiment of the present invention.

With continued reference to FIGS. 1 and 2, septum actuator 30 further comprises a probe portion 32 that extends proximally from base 34. Probe portion 32 is generally axially centered within fluid pathway 26. A distance between probe portion 32 and base 34 is selected to permit unhindered forward or distal movement of septum 40 over septum actuator 30. In some instance, the distance between probe portion 32 and base 34 is selected to limit forward movement of septum 40 within fluid pathway 26, thereby preventing over-penetration of probe portion 32 through the slit 42 septum 40.

Septum actuator 30 is generally tubular and comprises a lumen 36 that is in fluid communication with fluid pathway 26. In some instances, blood control septum 40 comprises a forward receptacle 44 and a rearward receptacle 46, wherein the forward and rearward receptacles are separated by a membrane 48 comprising slit 42. Forward receptacle 44 generally comprises an inner diameter and length that is configured to receive and house probe portion 32 of septum actuator 30. Accordingly, when slit 42 of septum 40 is biased into an open position, fluid may freely flow between lumen 36, fluid pathway 26 and catheter 50.

Prior to activation of septum 40, probe portion 32 is positioned within forward receptacle 44 at a position that is proximate to membrane 48. Slit 42 of septum 40 is biased into an open position as septum 40 is slid within fluid pathway 26 in distal direction 14 over probe portion 32. In some instances, septum 40 is advanced in distal direction 14 as an external device 12 is inserted into fluid pathway 26 at proximal end 22, as shown in FIG. 3.

Figure 3:
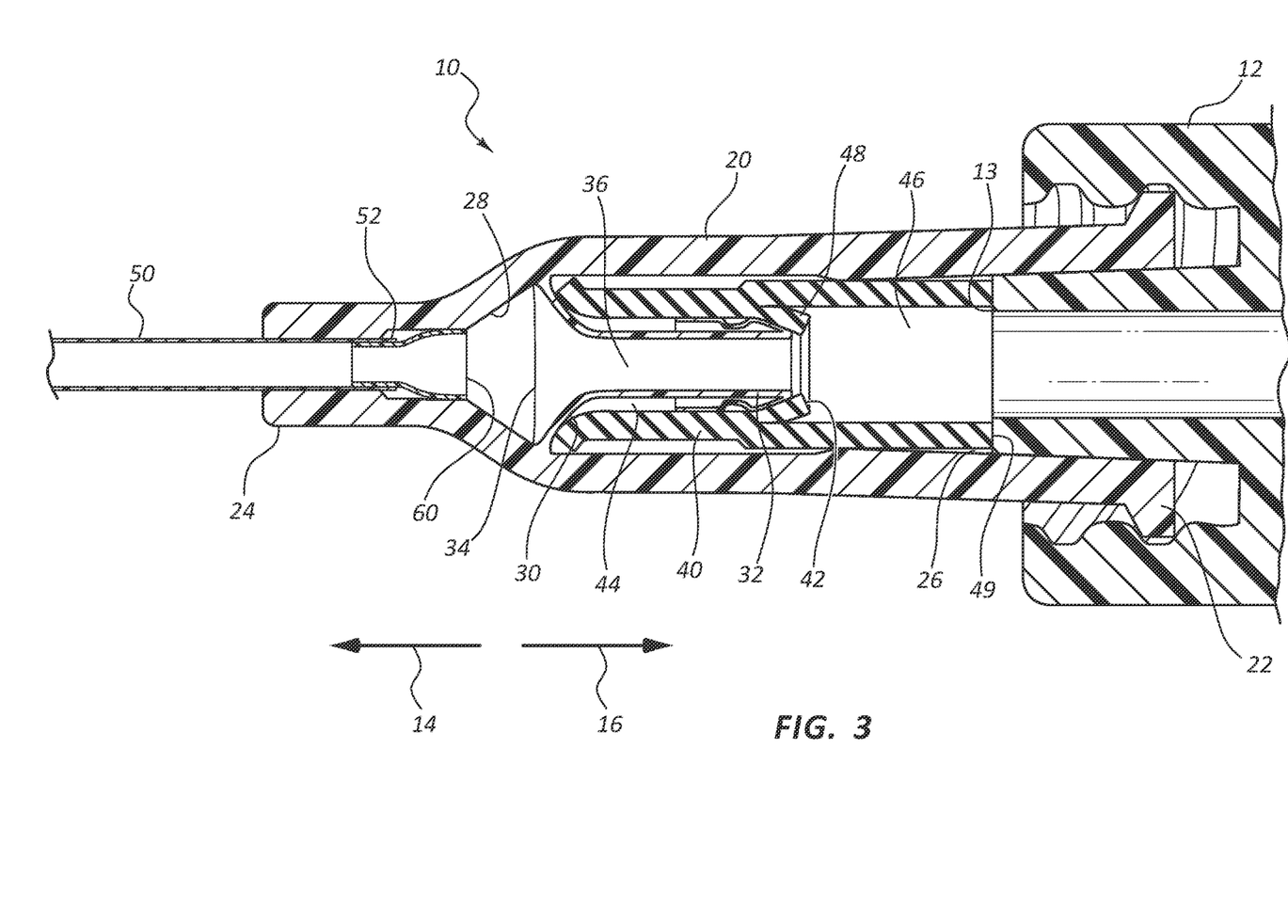
FIG. 3 is a cross-section side view of the catheter assembly of FIG. 1 following activation in accordance with a representative embodiment of the present invention.

With continued reference to FIG. 3, septum 40 is slid and repositioned distally within fluid pathway 26 as external device 12 is inserted into proximal end 22 of catheter adapter 20. A contact surface 13 of external device 12 is inserted into proximal end 22 to contact a proximal end surface 49 of septum 40. As contact surface 13 is advanced into fluid pathway 26, septum 40 slides in distal direction 14 thereby advancing septum 40 over probe portion 32 of septum actuator 30. Probe portion 32 biases slit 42 into an open position, thereby providing fluid communication between catheter 50, lumen 36, rearward receptacle 46, fluid pathway 26, and external device 12. Upon removal of external device 12, the resilient properties of septum 40 result in the self-closure of slit 42 thereby causing septum 40 to slide in proximal direction 16 to its initial starting position.

In some embodiments, probe portion 32 comprises a tapered outer surface to facilitate closure of slit 42 and retraction of septum 40 in proximal direction 16 following removal of external device 12. In other embodiments, inner surface 28 of catheter adapter 20 comprises one or more surface features to restrict or limit distal movement of septum 40. For example, in some embodiments inner surface 28 comprises a reduced diameter 54 that compresses the outer surface of septum 40 as septum 40 is advanced in distal direction 14. Following removal of external device 12, the compressive forces assist septum 40 in sliding in proximal direction 16 to resume its initial position.

Figure 4:
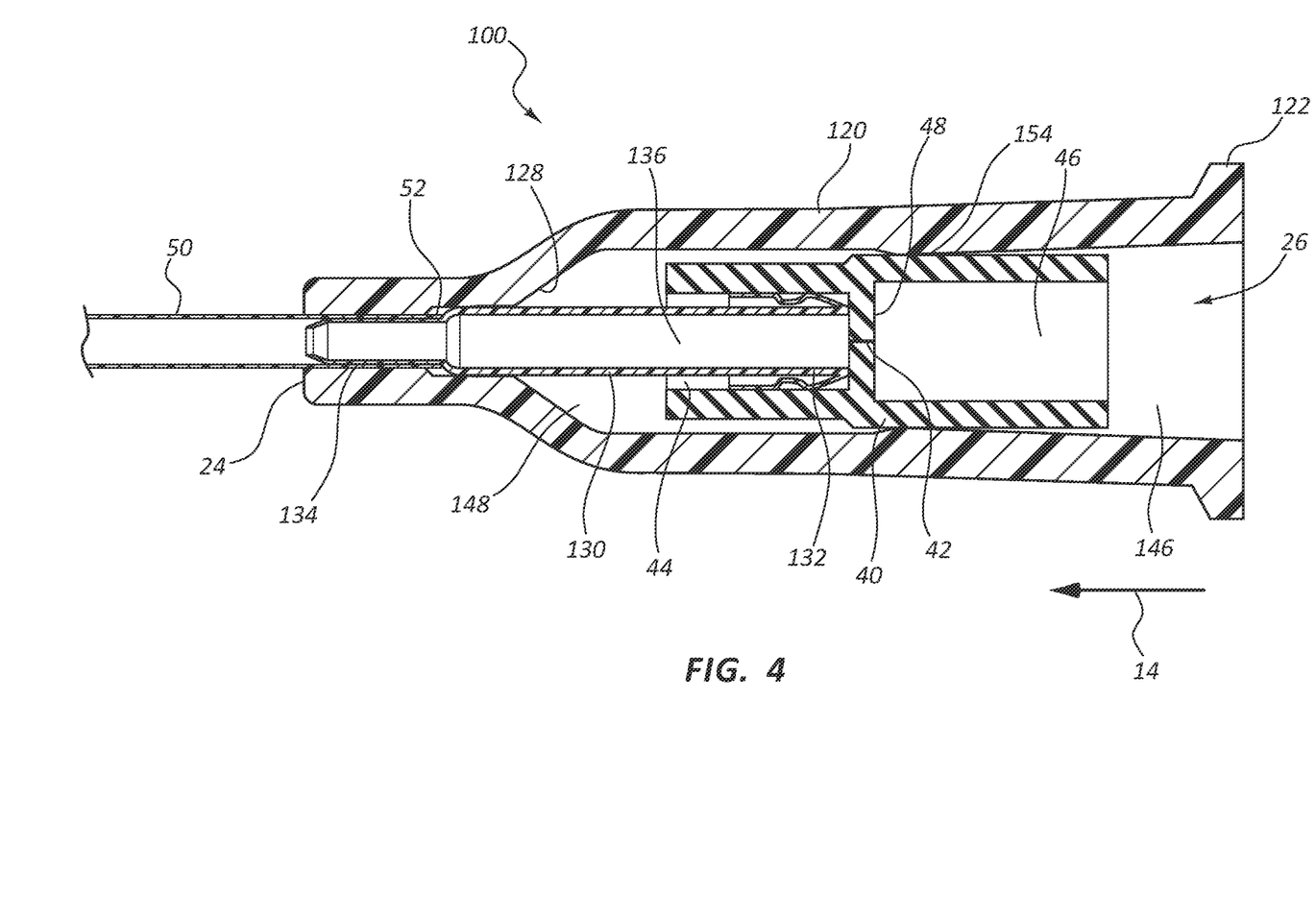
FIG. 4 is a cross-section side view of a catheter assembly comprising a septum actuator having a distal end comprising a wedge that is configured to fixedly couple a base portion of the catheter into the distal end of the catheter adapter, the septum actuator further comprising a probe that extends distally from the wedge and is positioned adjacent a blood control septum of the catheter assembly in accordance with a representative embodiment of the present invention.

Referring now to FIG. 4, a blood control catheter assembly 100 is shown. In some embodiments, catheter assembly 100 comprises a septum actuator 130 having a probe portion 132 and catheter wedge 134 interconnected via a lumen 136. Catheter wedge 134 is inserted into base 52 of catheter 50 to secure catheter 50 in distal end 24 of catheter adapter 20. Probe portion 132 extends outwardly from catheter wedge 134 towards proximal end 122 of catheter adapter 120. In some embodiments, probe portion 132 is approximately axially centered within fluid channel 26 of catheter adapter 120. Lumen 136 of septum actuator 130 interconnects probe portion 132 and catheter wedge 134 and provides fluid communication therebetween. The distance between probe portion 132 and catheter wedge 134 is generally selected to permit septum 40 to slide in distal direction 14 a distance sufficient to advance probe portion 132 through slit 42 of membrane 48, thereby providing fluid communication between catheter 50, lumen 136, rearward chamber 46, and fluid pathway 26.

In some instances, the distance between probe portion 132 and catheter wedge 134 is selected to prevent over-insertion of probe portion 132 through slit 42. For example, the distance between probe portion 132 and catheter wedge 134 may be selected to achieve contact between a distal end of septum 40 and inner wall surface 128 of catheter adapter 120 when a desired maximum penetration of probe portion 132 through slit 42 is achieved.

In some embodiments, septum 40 comprises an outer diameter that is slightly larger than a reduced diameter 154 of inner surface 128. Septum 40 forms a fluid tight seal with inner surface 128 at reduced diameter 154. As such, septum 40 divides fluid pathway 26 into a proximal fluid chamber 146 and a distal fluid chamber 148. In some instances, it is undesirable for fluid to leak into distal fluid chamber 148. Accordingly, catheter wedge 134 forms a fluid tight seal with base 52 of catheter 50. Further, an outer diameter of probe portion 132 is slightly larger than an inner diameter of forward receptacle 44. As such, a fluid tight seal is provided between probe portion 132 and septum 40 at forward receptacle 44.

Figure 5:
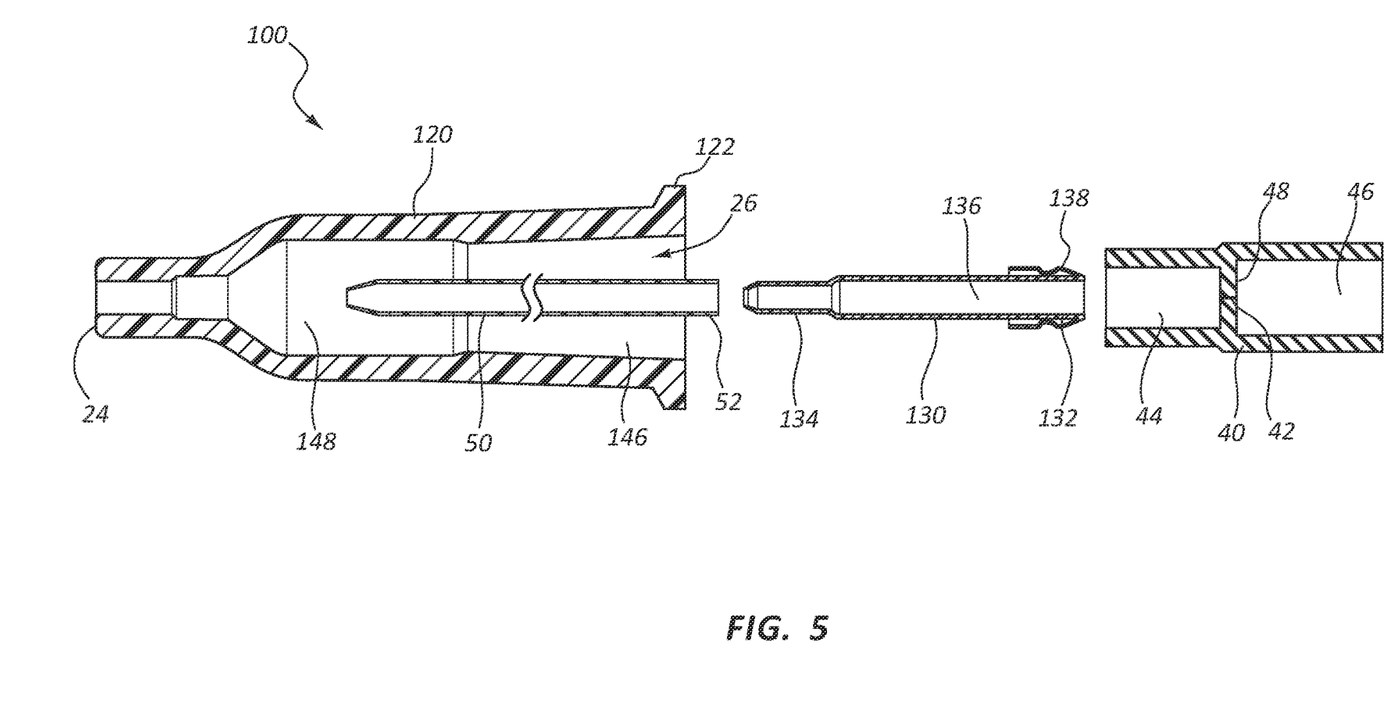
FIG. 5 is an exploded, cross-section view of the catheter assembly of FIG. 4 in accordance with a representative embodiment of the present invention.

Referring now to FIG. 5, an exploded view of catheter assembly 100 is shown. In some embodiments, catheter assembly 100 is assembled by first inserting catheter 50 into catheter adapter 120, such that base 52 of catheter 50 is positioned in distal end 24. Catheter 50 is secured to catheter adapter 120 by inserting catheter wedge 134 of septum actuator 130 into base 52. Catheter wedge 134 is configured to secure catheter 50 to catheter adapter 130 by inserting into catheter 50 and compressing base 52 between catheter wedge 134 and distal end 24. This compression fit provide a fluid tight seal between catheter 50 and septum actuator 130, thereby preventing leakage of fluids into distal fluid chamber 148. This fluid tight seal provides fluid communication between catheter 50 and lumen 136 of septum actuator 130.

Following the securement of catheter 50 and septum actuator 130, septum 40 is inserted into catheter adapter 120 at proximal end 122. Septum 40 is slid into catheter adapter 120 such that probe portion 132 of septum actuator 130 is inserted into forward receptacle 44. In some embodiments, septum 40 is positioned within fluid pathway 26 such that membrane 48 abuts probe portion 132.

Figure 6:
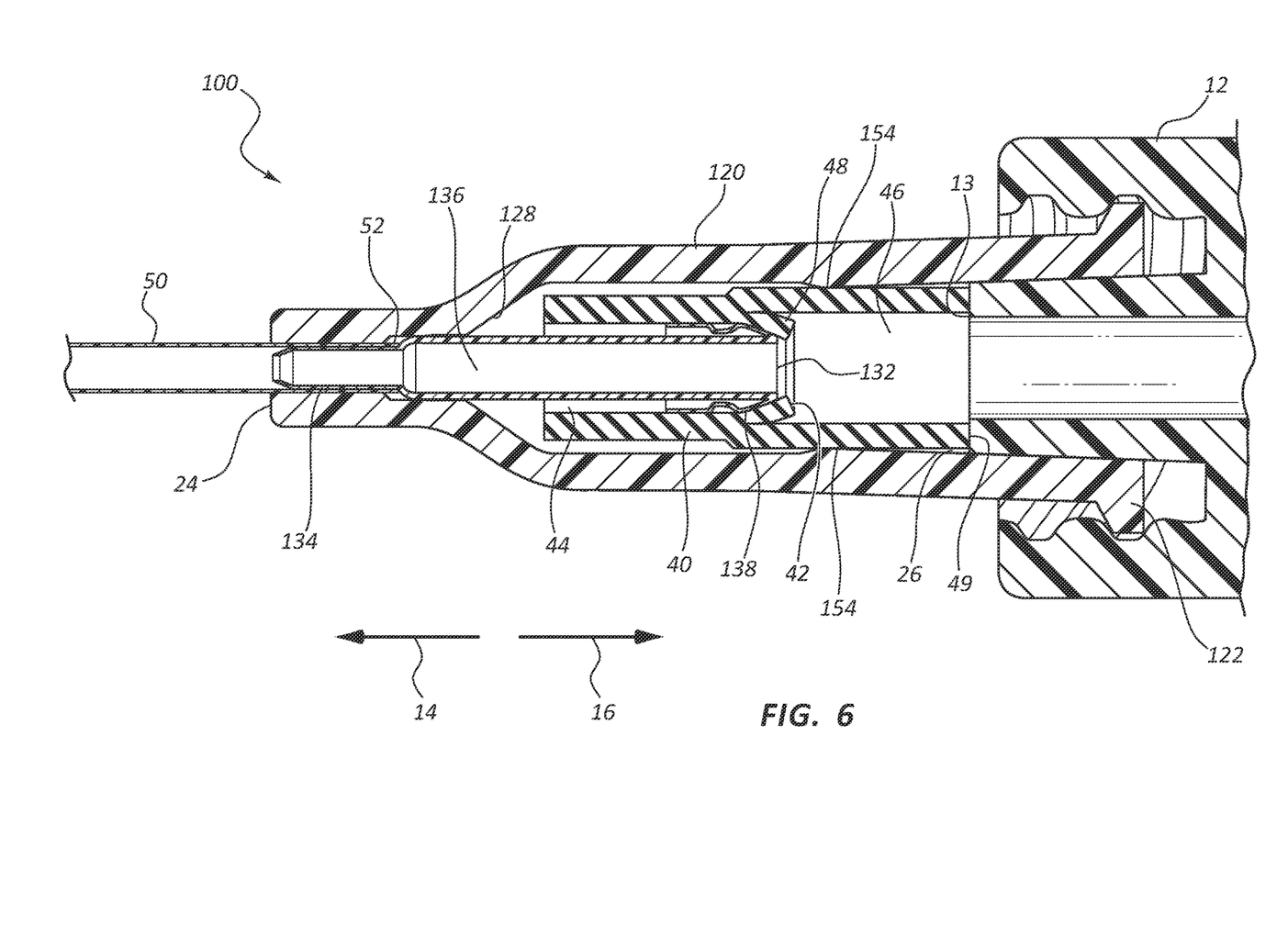
FIG. 6 is a cross-section side view of the catheter assembly of FIG. 4 following activation via a Luer adapter in accordance with a representative embodiment of the present invention.

Upon further movement of septum 40 in distal direction 14, probe portion 132 is advanced through slit 42 of membrane 48, thereby providing fluid communication between lumen 136 of septum actuator 130 and rearward receptacle 46 of septum 40, as shown in FIG. 6. For example, an external device 12, such as a Luer adapter, may be inserted into proximal end 122 to contact and advance septum 40 in distal direction 14. In some embodiments, probe portion 132 comprises a chamfered outer surface 138 that contacts membrane 48 and forms a fluid tight seal with upper and lower flaps of membrane 48. As such, fluid is prevented from leaking between membrane 48 and chamfered outer surface 138.

In some embodiments, a blood control catheter assembly of the present invention comprises one or more surfaces which may be coated with an anti-pathogenic material. An anti-pathogenic material may be provided to prevent colonization of pathogens on various components of the catheter assembly. Additionally, an anti-pathogenic material comprising a lubricant may be applied to various components of the catheter assembly to reduce friction between interfacing surfaces and prevent colonization of pathogens at the interface.

In some instances, an anti-pathogenic material is first applied to inner surfaces 28/128 prior to assembling the catheter assembly. In this way, the anti-pathogenic material is transferred from inner surface 28/128 to the various other components during assembly and use. In other instances, an anti-pathogenic material is applied to the various components of the catheter assembly prior to be inserted into the catheter adapter. In this way, anti-pathogenic material is transferred from the various components to the catheter adapter during assembly and use.

In some embodiments, inner surface 28/128 is coated with a rigid or semirigid anti-pathogenic material such that fluid that flows through fluid pathway 26 comes in contact with the anti-pathogenic material. As such, bacterial colonization on the coated surfaces is prevented. The rigid or semi-rigid properties of the anti-pathogenic material prevent easy removal of the coating from the surface. Thus, the surface remains coated for a duration of effectiveness of the anti-pathogenic material. In some instances, the rigid or semi-rigid properties of the anti-pathogenic material allows a surface to be coated without interfering with a critical dimension of the surface, as taught in U.S. patent application Ser. No. 13/471,716.

In other embodiments, inner surface 28/128 is coated with a viscous or fluid anti-pathogenic material comprising a lubricious agent, such as silicon oil. In some instances, the lubricious coating is provided on interface surfaces between septum 40 and inner surface 28/128. Septum 40 may comprises a material that exhibits high friction when moving against a polymer surface, such as inner surface 28/128. For example, septum 40 may comprise a silicon material that exhibits "sticky" characteristics when septum 40 is moved within fluid chamber 26 of catheter adapter 120. Thus, in some embodiments it is advantageous to place a lubricous anti-pathogenic material between the interfacing surfaces of the septum 40 and catheter adapter 120 to facilitate the slideable movement of septum 40 within catheter adapter 120. Accordingly, an anti-pathogenic coating material of the present invention may include a lubricant to achieve this benefit.

Figure 7:
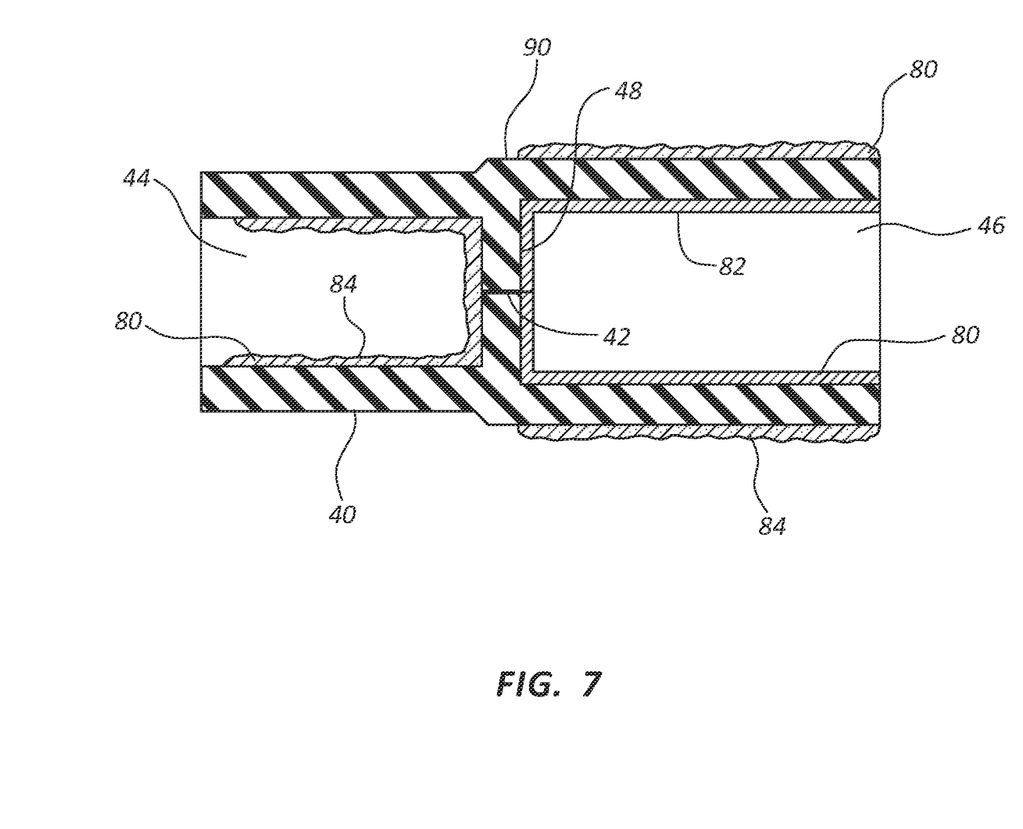
FIG. 7 is a cross-section side view of a blood control septum having lubricious and non-lubricious anti-pathogenic material applied at various surfaces having critical and non-critical dimensions in accordance with a representative embodiment of the present invention.

Referring now to FIG. 7, in some embodiments an anti-pathogenic material 80 is applied to various surfaces of septum 40 prior to assembling catheter assembly 10. For example, a rigid anti-pathogenic material 82 may be preferred for use on surfaces of septum 40 that are in direct contact with fluids flowing through catheter assembly 10. In some instances, a rigid anti-pathogenic material 82 may be applied to rearward receptacle 46, wherein rearward receptacle 46 is in direct contact with fluid during use of catheter assembly 10. Rigid anti-pathogenic material 82 is generally more resistant to wear, and therefore may be applied to surfaces that are susceptible to wear, such as surfaces that are in direct contact with fluid. Rigid anti-pathogenic material 82 may also comprise a thin layer which is applied to surfaces having a critical dimension. For example, rearward receptacle 46 may have a diameter that is critical to facilitate proper fluid flow dynamics through septum 40. Alternatively, rearward receptacle 46 may have a diameter that is critical to receive a portion of an external device.

Septum 40 may further comprise a lubricious anti-pathogenic material 84 that is applied to various surfaces of septum 40 to reduce friction between septum 40 and a surface of another device or component of the catheter assembly. For example, in some embodiments a lubricious anti-pathogenic material 84 is applied to an outer surface 90 of septum 40 to reduce friction between septum 40 and the inner surface of the catheter adapter. Further, a lubricious anti-pathogenic material 84 may be applied to an inner surface of forward receptacle 44 to reduce friction between septum 40 and probe portion 132 of septum actuator 130. In addition to reducing friction, lubricious anti-pathogenic material 84 provides anti-pathogenic properties to septum 40 to prevent colonization of pathogens.

In some embodiments, the fluid nature of lubricious anti-pathogenic material 84 permits transfer of lubricious anti-pathogenic material 84 from septum 40 to other surfaces in contact with septum 40. For example, in some embodiments anti-pathogenic material 84 deposited in forward receptacle 44 is transferred to septum actuator 130 as the septum actuator is positioned within forward receptacle 44. Additionally, as the septum actuator is advanced through slit 42 of septum 40, lubricious anti-pathogenic material 84 may be transferred to additional surfaces of the septum actuator. Further still, lubricious anti-pathogenic material 84 on outer surface 90 of septum 40 may be transferred to the inner surface of the catheter adapter as septum 40 is slid distally and proximally within fluid channel 26 of the catheter adapter. In some instances, lubricious anti-pathogenic material 84 is further transferred to various surfaces of external device 12 as external device 12 is inserted into the catheter adapter to advance septum 40 in distal direction 14. Transfer of anti-pathogenic material 84 to external device 12 may reduce friction between external device 12 and the catheter adapter. Transfer of anti-pathogenic material 84 to external device 12 may further prevent colonization of pathogens on external device 12 and generally within fluid pathway 26. Rigid 82 and lubricious 84 anti-pathogenic materials may further be transferred to septum actuator 30 of catheter assembly 10, in accordance with the methods discussed above.

Figure 8:
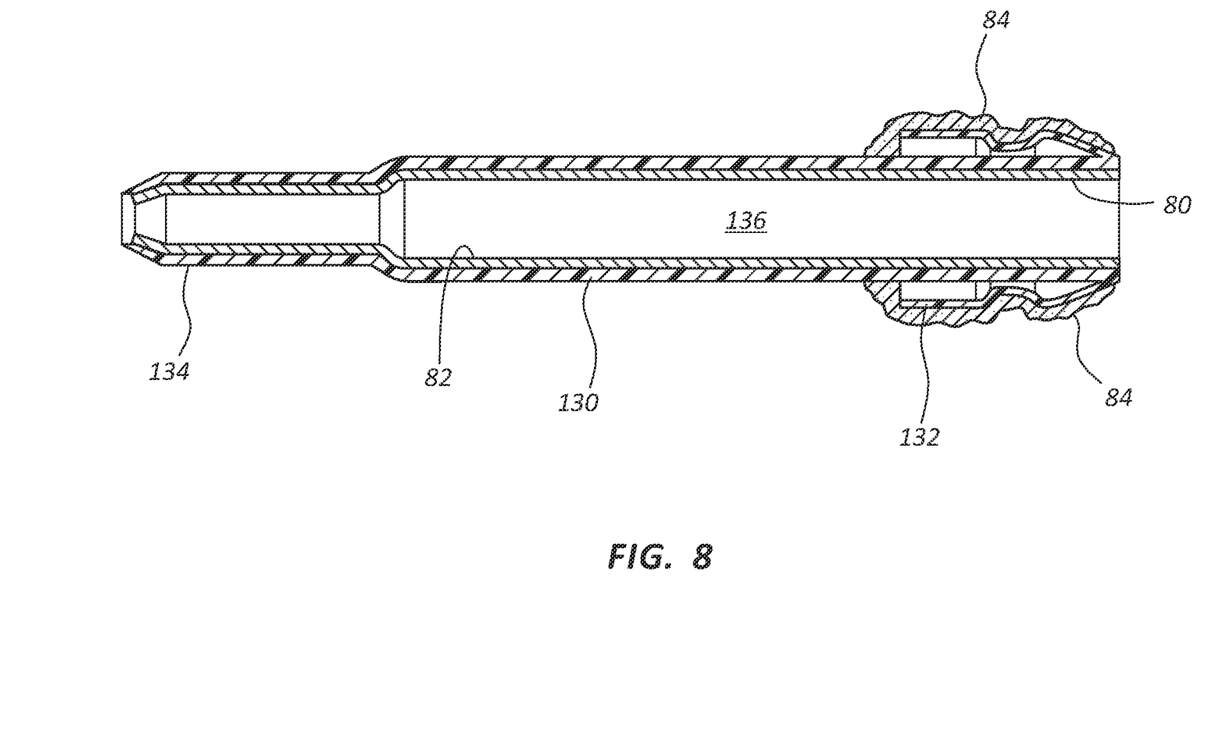
FIG. 8 is a cross-section view of a septum actuator having a distal end comprising a wedge that is configured to fixedly couple a base portion of a catheter into a distal end of a catheter adapter, the septum actuator further comprising a probe that extends distally from the wedge so as to be positioned adjacent a blood control septum of a catheter assembly, the septum actuator having lubricious and non-lubricious material applied at various surfaces having critical and non-critical dimensions in accordance with a representative embodiment of the present invention.

Referring now to FIG. 7, in some embodiments rigid 82 and lubricious 84 anti-pathogenic materials are applied to various surfaces of septum actuator 130 prior to assembly of the catheter assembly. For example, in some instances a rigid anti-pathogenic material 82 is applied to the inner surface of septum actuator 130, so as to be in contact with fluid flowing through lumen 136. Further, a lubricious anti-pathogenic material 84 is applied to probe portion 132 of septum actuator 130. Lubricious anti-pathogenic material 84 reduces friction between probe portion 132 and forward receptacle 44 as septum 40 is slid in distal direction 14 within the catheter adapter. Lubricious anti-pathogenic material 84 further reduces friction between probe portion 130 and membrane 48 to facilitate easy insertion of probe portion 130 through slit 42 of membrane 48. Rigid and lubricous anti-pathogenic materials 82 and 84 may also be applied to septum actuator 30 of catheter assembly 10, in accordance with the methods discussed above.

In some embodiments, the fluid nature of lubricious anti-pathogenic material 84 permits transfer of lubricious anti-pathogenic material 84 from septum actuator 130 to other surfaces in contact with septum actuator 130. For example, in some embodiments anti-pathogenic material 84 deposited or coated onto probe portion 132 of septum actuator 130 is transferred to forward receptacle 44 as septum actuator 130 is inserted into forward receptacle 44 during assembly. Additionally, as septum actuator is advanced through slit 42 of septum 40, lubricious anti-pathogenic material 84 may be transferred to additional surfaces of septum 40, such as membrane 48 and slit 42. In some instances, lubricious anti-pathogenic material 84 is transferred from probe portion 132 to slit 42, thereby further providing a fluid tights seal for slit 42.

In some instances, lubricious 84 and rigid 82 anti-pathogenic materials are applied to both the septum and the septum actuator prior to assembling the catheter assembly. In other instances, excess lubricious anti-pathogenic material 84 is applied to the septum and septum actuator with the intention of transferring the excess anti-pathogenic material to various surfaces of the catheter assembly when the various components of the catheter assembly are assembled.

In general, the anti-pathogenic materials of the present invention may be applied to any internal or external surface of a medical device, or a component of a medical device, wherein the surface comprises or is exposed to a fluid pathway through the medical device. The surface may further include a critical or non-critical dimension. Pathogens within a fluid passing through the medical device are thus prevented from colonizing within the medical device. In some embodiments, the thickness of the anti-pathogenic material is proportionate to a duration of effectiveness of the anti-pathogenic material on the coated surface. Thus, the duration of effectiveness of the coating may be increased by increasing the thickness of the anti-pathogenic material applied to the surface. The duration of effectiveness may further be modified through modifying the physical properties of the anti-pathogenic material to increase or decrease the rate at which the anti-pathogenic agents are capable of eluting out of the coating material.

In some embodiments, a rigid or semirigid anti-pathogenic material 82 is selected which is configured to permit long-term elution of the anti-pathogenic agents contained within the material 82. As such, it is desirable to provide the anti-pathogenic material to much of the fluid path surface area of catheter assembly. In other embodiments, a viscous, fluid anti-pathogenic material 84 is selected which further comprises a lubricant agent. For example, in some embodiments a lubricious anti-pathogenic material 84 is provided which further includes a silicon lubricant agent, such as MED-460 (manufactured by NuSil Technology, LLC). The inclusion of a lubricious agent reduces friction between interfacing components of catheter assembly. In some embodiments, the lubricous anti-pathogenic material 84 further provides a fluid-tight seal between the various components of the catheter assembly.

In some embodiments, lubricous anti-pathogenic material 84 comprises a modified rheology to prevent or control excessive migration of the lubricous anti-pathogenic material within the catheter assembly. For example, lubricous anti-pathogenic material 84 may further include rheological modifiers to increase the viscosity of the material, such as silica, talc or clay.

The process for coating or applying the anti-pathogenic materials to compatible surfaces of the catheter assembly may be accomplished by dipping the desired portions or components of the device in their respective coating material 82 and/or 64. Alternatively, anti-pathogenic materials may be sprayed onto the desired surfaces. In some embodiments, surfaces having critical dimensions are masked or otherwise protected prior to applying the anti-pathogenic material to the remaining surfaces. Compatible surfaces may further include a mechanical feature to encourage mechanical binding between the coating material and the compatible surface.

For example, a compatible surface may be designed to include a physical feature that increases mechanical binding of the coating material, such as a texture, a groove, a ridge or some other feature which increases the surface area of the compatible surface. In some embodiments, a mechanical bond is facilitated by a mechanical interlock comprising a void which holds the anti-pathogenic material by capillary force or surface tension forces. In other embodiments, a mechanical interlock comprises a hydrophilic or hydrophobic material or coating that is applied to the compatible surface to attract the anti-pathogenic material.

Further, in some embodiments the anti-pathogenic material is chemically bound to the compatible surface of the catheter assembly or medical device by a chemical bond, such as surface cross-linking. For example, in some embodiments a compatible surface of a device comprises a polymer material that is capable of forming chemical bonds with at least one component of an anti-pathogenic material. Non-limiting examples of polymer materials which may be used to achieve surface cross-linking include polycarbonate, polyester, and polyurethane. In some instances, an anti-pathogenic material is applied to a compatible surface of a device and then cured to achieve surface cross-linking between the anti-pathogenic material and the surface of the device.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The various embodiments of the present invention may be adapted for use with any medical device or accessory having a lumen in which is seated a septum. For example, in some embodiments a female Luer adapter coupled to a section of intravenous tubing may comprise a septum and a septum actuator in accordance with the present teachings. In other embodiments, one or more ends of a y-port adapter may comprise a septum and a septum actuator in accordance with the teachings of the present invention.

The invention claimed is:

1. A catheter assembly, comprising:
a catheter adapter having a proximal opening, a distal end, and a fluid pathway extending therebetween, the distal end of the catheter adapter housing a catheter, wherein the catheter adapter includes a tapered portion, wherein an inner surface of the tapered portion tapers gradually toward the distal end;
a septum slidably disposed within the fluid pathway, the septum having an H-shaped cross-section forming a distal receptacle, a proximal receptacle, and a membrane that separates the distal receptacle from the proximal receptacle, wherein the distal receptacle includes an upper arm and a lower arm;
a septum actuator positioned within the distal receptacle, the septum actuator having a central lumen that extends towards the proximal end of the catheter adapter, the septum actuator having a probe configured to bias the septum into an open position by opening a pathway through the membrane of the septum to allow fluid to flow through the septum when the septum is advanced within the fluid pathway towards the distal end of the catheter adapter such that the fluid pathway flows through the central lumen of the septum actuator and through the septum when the probe biases the septum into the open position, wherein a distal end of the septum actuator includes a base, wherein the probe extends proximally from the base of the septum actuator, wherein an inner diameter of a portion of the central lumen that extends through the base is larger than an inner diameter of a portion of the fluid pathway extending through probe, wherein the base is fixedly secured to the tapered portion of the catheter adapter, wherein the upper arm and the lower arm are configured to contact the base to splay outwardly in response to the entire septum sliding distally into the open position;
wherein inserting an external device into the proximal opening of the catheter adapter slides the entire septum distally into the open position and wherein removing the external device allows the membrane to self-close to slide the entire septum proximally into a closed position wherein the upper and lower arms extend parallel to each other in the closed position.

2. The catheter assembly of claim 1, further comprising an anti-pathogenic material applied to the septum actuator at an interface surface between the septum actuator and the septum.

3. The catheter assembly of claim 2, wherein the anti-pathogenic material comprises a lubricant.

4. The catheter assembly of claim 1, wherein at least one of the catheter adapter, the septum, and the septum actuator further comprise a surface exposed to the fluid pathway.

5. The catheter assembly of claim 4, further comprising an anti-pathogenic material applied to the surface exposed to the fluid pathway.

6. The catheter assembly of claim 5, wherein the anti-pathogenic material comprises a lubricant.

7. The catheter assembly of claim 1, further comprising an anti-pathogenic material applied to an outer surface of the septum at an interface surface between the septum and an inner surface of the catheter adapter.

8. The catheter assembly of claim 7, wherein the anti-pathogenic material comprises a lubricant.

9. The catheter assembly of claim 8, wherein the lubricant is a silicon-based lubricant.

10. The catheter assembly of claim 2, wherein the anti-pathogenic material is rigid or semi-rigid.

11. The catheter assembly of claim 7, wherein the anti-pathogenic material is rigid or semi-rigid.

12. The catheter assembly of claim 2, further comprising an identifying color to indicate a specific type of the anti-pathogenic material.

13. The catheter assembly of claim 2, wherein the anti-pathogenic material is applied to the septum actuator at a desired thickness that is proportionate to a duration of effectiveness of the anti-pathogenic material on the interface surface.

14. The catheter assembly of claim 2, wherein the anti-pathogenic material is in communication with a portion of the fluid pathway.

* * * * *